(12) United States Patent
Yang et al.

(10) Patent No.: US 11,021,483 B2
(45) Date of Patent: Jun. 1, 2021

(54) CRYSTALLINE OF CAMPHORSULFONIC ACID SALT OF RUCAPARIB AND METHOD OF PREPARING OF TRICYCLIC COMPOUNDS, RUCAPARIB AND CRYSTALLINE OF CAMPHORSULFONIC ACID SALT OF RUCAPARIB

(71) Applicant: Formosa Laboratories, Inc., Taoyuan (TW)

(72) Inventors: Wen-Chieh Yang, Taichung (TW);
Mei-Jing Lee, Taipei (TW);
Hsueh-Chen Lee, Miaoli (TW);
Lung-Hsiang Li, Taipei (TW)

(73) Assignee: Formosa Laboratories, Inc., Taoyuan (TW)

( * ) Notice: Subject to any disclaimer, the term of this patent is extended or adjusted under 35 U.S.C. 154(b) by 0 days.

(21) Appl. No.: 16/529,224

(22) Filed: Aug. 1, 2019

(65) Prior Publication Data

US 2020/0165261 A1    May 28, 2020

(30) Foreign Application Priority Data

Nov. 27, 2018    (CN) .......................... 201811423037.X

(51) Int. Cl.
*C07D 471/06*    (2006.01)
*C07D 487/06*    (2006.01)

(52) U.S. Cl.
CPC ........ *C07D 487/06* (2013.01); *C07B 2200/13* (2013.01)

(58) Field of Classification Search
CPC .. C07D 487/06; C07D 471/06; C07B 2200/13
USPC ............................................. 540/520; 546/84
See application file for complete search history.

(56) References Cited

U.S. PATENT DOCUMENTS 6,977,298 B2    12/2005    Webber et al.
8,754,072 B2 *    6/2014    Basford ............... C07D 487/06
                                                    514/212.06

OTHER PUBLICATIONS

Afanasyev et al., Chem. Rev. 2019, 119, 11857-11911.*
Gillmore, et al., "Multkilogram Scale-Up of a Reductive Alkylation Route to a Novel PARP Inhibitor", American Chemical Society, dx.doi.org/10.1021/op200238p, Org. Process Res. Dev., 2012, 16, 1897-1904.

* cited by examiner

*Primary Examiner* — Bruck Kifle
(74) *Attorney, Agent, or Firm* — Fay Sharpe LLP

(57) ABSTRACT

A method of preparing a tricyclic compound of formula (I), comprising the step of converting a compound of formula (II) into a compound of formula (III); and hydrogenating the compound of formula (III) in the presence of hydrogenation catalyst and hydrogen to form the tricyclic compound of formula (I); wherein $R_1$ is H or a $C_{1-3}$ alkyl group; and $R_2$ is H, a halogen element or a $C_{1-3}$ alkyl group.

15 Claims, 4 Drawing Sheets

CRYSTALLINE OF CAMPHORSULFONIC ACID SALT OF RUCAPARIB AND METHOD OF PREPARING OF TRICYCLIC COMPOUNDS, RUCAPARIB AND CRYSTALLINE OF CAMPHORSULFONIC ACID SALT OF RUCAPARIB

CROSS-REFERENCE TO RELATED APPLICATION

This application claims priority to CN application No. 201811423037.X filed on Nov. 27, 2018, which is herein incorporated by reference in its entirety.

BACKGROUND

The present invention is related to a method of preparing of tricyclic compounds. More particularly, the present invention is related to a method of preparing of tricyclic compounds for PARP inhibitor. The present invention is further related to a method of preparing of Rucaparib and related to crystalline of (S)-camphorsulfonate salt of Rucaparib as well as a method of preparing the same.

DESCRIPTION OF RELATED ART

PARP (Poly(ADP-ribose) polymerase) is one kind of enzyme families participating the repair of DNA. According to recent research, PARP inhibitor is a new chemotherapeutic agent for treating various cancers. Also, Rucaparib is a PARP inhibitor for treatment of advanced ovarian cancer specifically associated with BRCA mutations.

As to the synthetic method of Rucaparib in U.S. Pat. No. 6,977,298, it discloses a synthesis scheme as shown in FIG. 1. Rucaparib with structure of formula (1) is produced from the compound of formula (2) through multiple synthetic steps and purification steps. Specifically, the compound of formula (2) is reacted with methylamine to obtain the compound of formula (3). Thereafter, the compound of formula (3) is reacted with a reducing agent NaBH$_3$CN, and then hydrochloric acid is added therein to quench the reaction, and subsequently a purification step is carried out to obtain the compound of formula (4). Finally, the compound of formula (4) is reacted with KOH to obtain the Rucaparib of formula (1).

In the aforesaid conventional synthesis, a plurality of synthetic steps and purification steps are required to obtain the Rucaparib of the formula (1). Accordingly, the complicated synthetic steps greatly reduce the total yield and take more time. Moreover, in the above conventional synthesis, NaBH$_3$CN as reducing agent is used to reduce imine compounds (i.e., the compound of formula (3)) and toxic HCN gas is therefore generated in the process of reaction, which is disadvantageous for production in a large scale.

SUMMARY

According to one embodiment of the present disclosure, the present invention provides a method of preparing a tricyclic compound of formula (I) below.

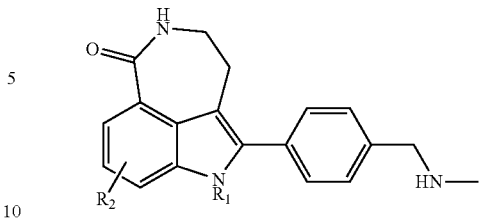

formula (I)

The method comprises steps of:
(i) converting a compound of formula (II) into a compound of formula (III);

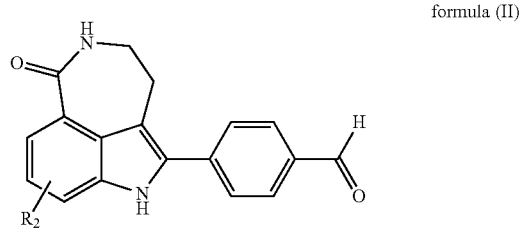

formula (II)

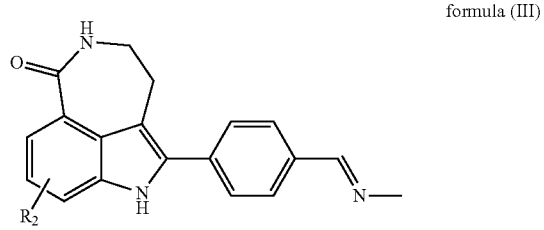

formula (III)

(ii) hydrogenating the compound of formula (III) under hydrogen to produce the tricyclic compound of formula (I) in the presence of a hydrogenation catalyst, in which R$_1$ is H or a C$_{1-3}$ alkyl group and R$_2$ is H, a halogen element or a C$_{1-3}$ alkyl group.

In one embodiment of the present disclosure, the step of converting the compound of formula (II) into the compound of formula (III) comprises reacting the compound of formula (II) with methylamine to form the compound of formula (III).

In one embodiment of the present disclosure, the hydrogenated catalyst in the step of hydrogenating the compound of formula (III) is at least one selected from the group consisting of Pd catalyst, Ni catalyst, Pt catalyst and Rh catalyst.

In one embodiment of the present disclosure, the hydrogenation catalyst in the step of hydrogenating the compound of formula (III) to produce the tricyclic compound of formula (II) is Pd/C catalyst.

In one embodiment of the present disclosure, the step of converting the compound of formula (II) and the step of hydrogenating the compound of formula (III) are performed in succession without isolating the compound of formula (III).

In one embodiment of the step before converting the compound of formula (II) in the present disclosure, the method of preparing the tricyclic compound of formula (I) further comprises a step of reacting a compound of formula (IV) with a compound of formula (V) to form the compound of formula (II), in which X is a halogen element.

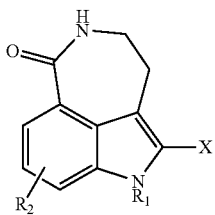

formula (IV)

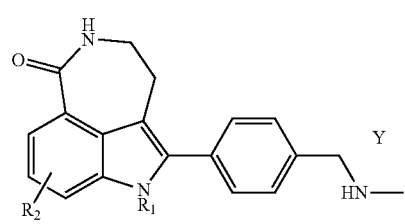

formula (X)

wherein Y is a pharmaceutically acceptable acid.

The method comprises steps of:

(i) preparing a tricyclic compound of formula (I) using the method described above; and

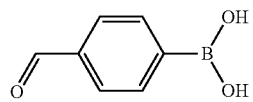

formula (V)

In one embodiment of the step before reacting the compound of formula (IV) with the compound of formula (V) in the present disclosure, the method of preparing the tricyclic compound of formula (I) further comprises a step of halogenating a compound of formula (VI) to produce the compound of formula (IV) below.

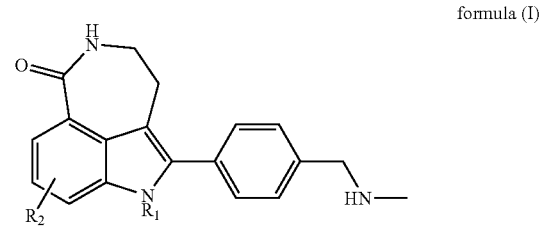

formula (I)

(ii) reacting the tricyclic compound of formula (I) with a pharmaceutically acceptable acid to form the tricyclic compound of formula (X), in which $R_1$ is H or a $C_{1-3}$ alkyl group and $R_2$ is H, a halogen element or a $C_{1-3}$ alkyl group and Y is a pharmaceutically acceptable acid.

In one embodiment of the present disclosure, the pharmaceutically acceptable acid is camphorsulfonic acid.

Another embodiment of the present disclosure is to provide a method of preparing Rucaparib of formula (I).

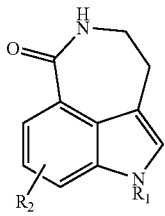

formula (VI)

In one embodiment of the step before halogenating the compound of formula (VI) in the present disclosure, the method of preparing the tricyclic compound of formula (I) further comprises a step of converting a compound of formula (VII) into the compound of formula (VI) below.

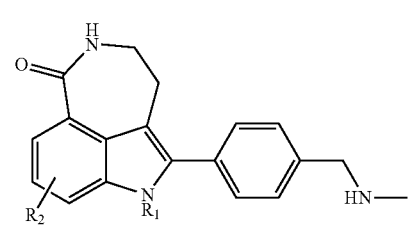

formula (I)

The method comprises the steps of:

(i) reacting a compound of formula (6) with a compound of formula (IX) to produce a compound of formula (7);

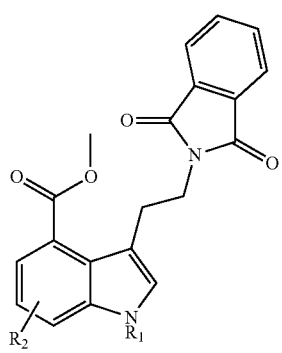

formula (VII)

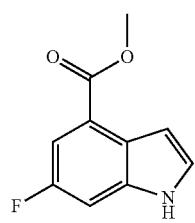

formula (6)

Another embodiment of the present disclosure is to provide a method of preparing a tricyclic compound of formula (X).

formula (IX)

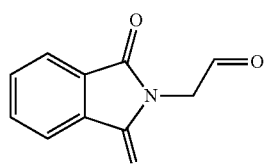

formula (2)

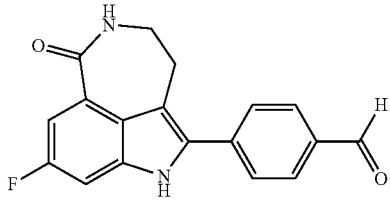

(V) converting the compound of formula (2) to form a compound of formula (3); and formula (7)

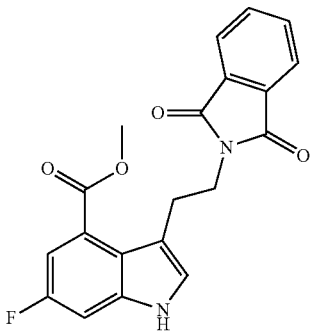

formula (3)

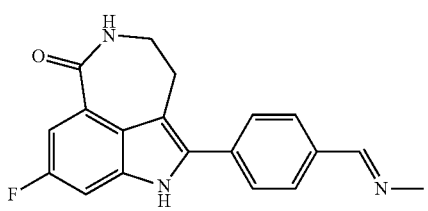

(ii) converting the compound of formula (7) to a compound of formula (8);

(Vi) hydrogenating the compound of formula (3) under hydrogen in the presence of hydrogenation catalyst to produce the Rucaparib of formula (1).

Another embodiment of the present disclosure is to provide a crystalline of a Rucaparib (S)-camphorsulfonate salt of formula (5), formula (8)

formula (5)

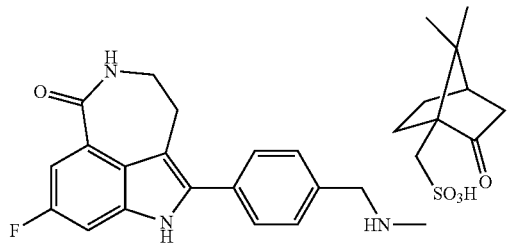

(iii) converting the compound of formula (8) to a compound of formula (9);

wherein the Rucaparib (S)-camphorsulfonate salt of formula (5) has a X-ray powder diffraction pattern comprising characteristic peaks at two theta vales of 6.0°±0.2°, 6.2°±0.2°, 12.2°±0.2° and 13.5°±0.2°.

formula (9)

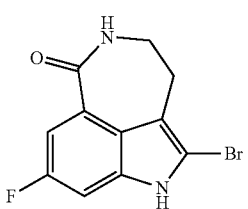

In one embodiment of the present disclosure, wherein the X-ray powder diffraction pattern further comprises characteristic peaks at two theta vales of 12.0°±0.2° and 25.7°±0.2°.

In one embodiment of the present disclosure, wherein the X-ray powder diffraction pattern further comprises characteristic peaks at two theta vales of 12.8°±0.2°, 14.8°±0.2°, 20.6°±0.2° and 25.1°±0.2°.

(iv) reacting the compound of formula (9) with a compound of formula (V) to form a compound of formula (2);

In one embodiment of the present disclosure, wherein the X-ray powder diffraction pattern is substantially the same as that shown in FIG. 3.

In one embodiment of the present disclosure, the melting point of crystalline of the Rucaparib (S)-camphorsulfonate salt of formula (5) is about 304±2° C.

formula (V)

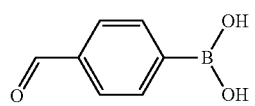

Another embodiment of the present disclosure is to provide a method of producing a Rucaparib (S)-camphorsulfonate salt of formula (5).

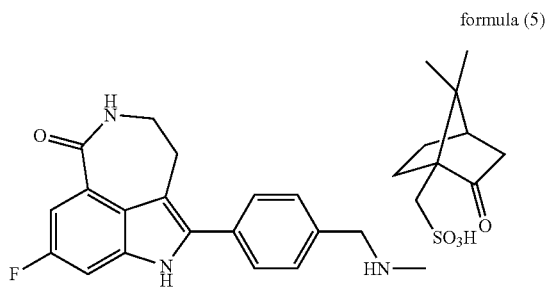

formula (5)

The method comprises steps of:

(i) reacting a Rucaparib of formula (1) with a (S)-camphorsulfonic acid in a methanol/water solution to form the Rucaparib (S)-camphorsulfonate salt of formula (5); and

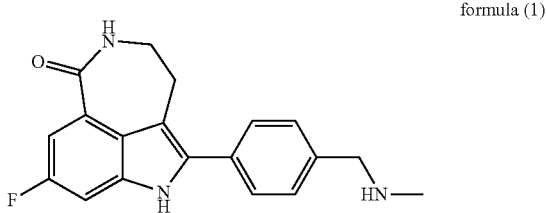 [SMILES: CNCc1ccc(-c2[nH]c3cc(F)cc4c3c2CCNC4=O)cc1]

formula (1)

(ii) filtrating a crystalline of the Rucaparib (S)-camphorsulfonate salt of formula (5) from the methanol/water solution, wherein the crystalline of Rucaparib (S)-camphorsulfonate salt of formula (5) has a X-ray powder diffraction pattern comprising characteristic peaks at two theta values of 6.0°±0.2°, 6.2°±0.2°, 12.2°±0.2° and 13.5°±0.2°.

DETAILED DESCRIPTION

Figure 1:
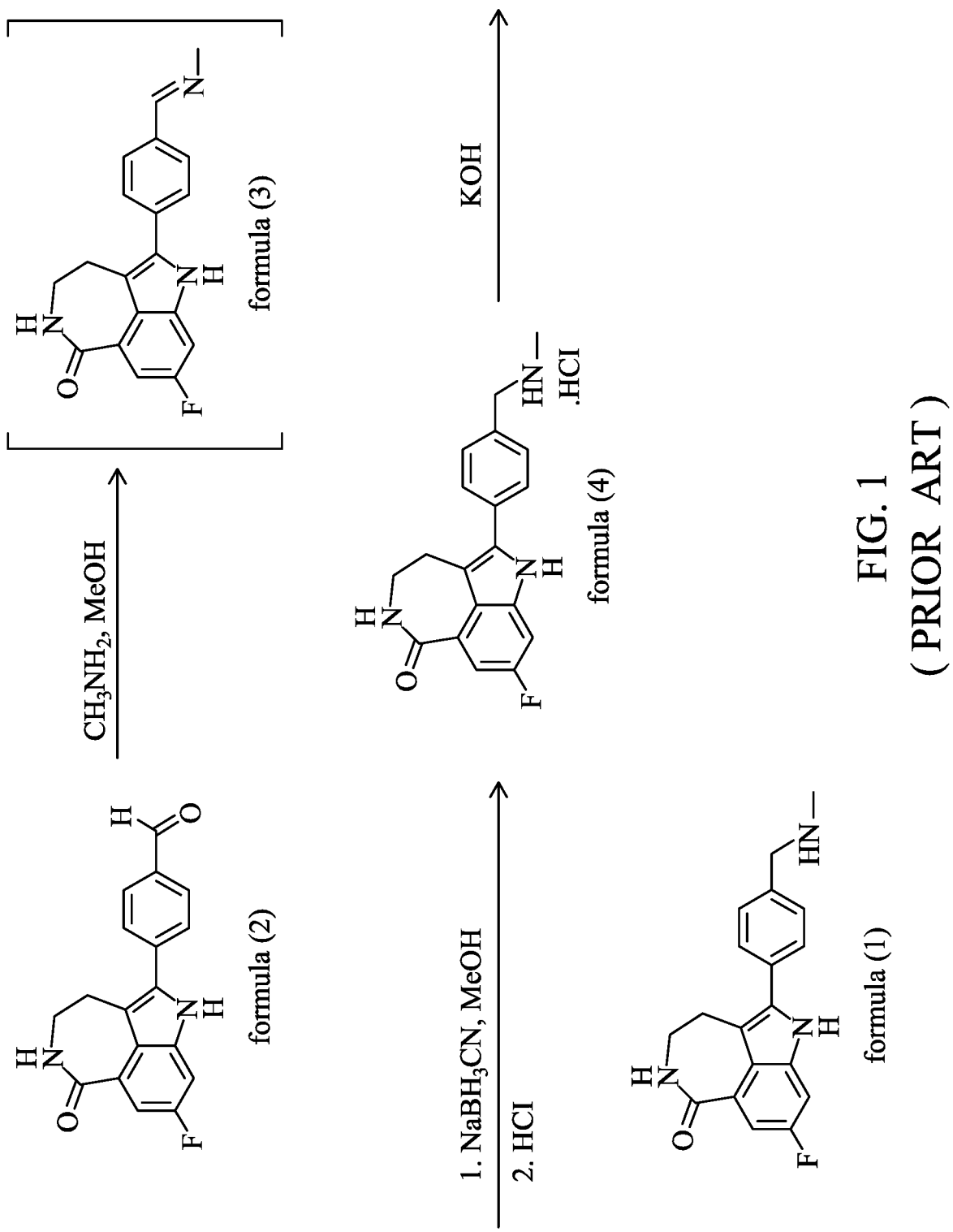
FIG. 1 shows a conventional synthesis scheme of Rucaparib.

The following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

One embodiment of the present disclosure provides a method of preparing PARP inhibitor. PARP inhibitor as the present disclosure has the following structure of formula (I):

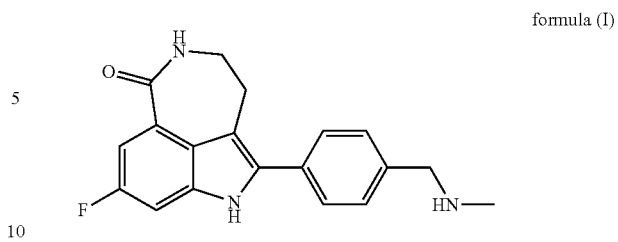

formula (I)

wherein $R_1$ is H or a $C_{1-3}$ alkyl group; and
$R_2$ is H, a halogen element or a $C_{1-3}$ alkyl group. Halogen is fluorine, chlorine, bromine or iodine.

In accordance with various embodiments of the present disclosure, the method of preparing of the tricyclic compound (i.e., PARP inhibitor) of formula (III) includes the following steps:

converting the following compound of formula (II) to form the following compound of formula (I); and

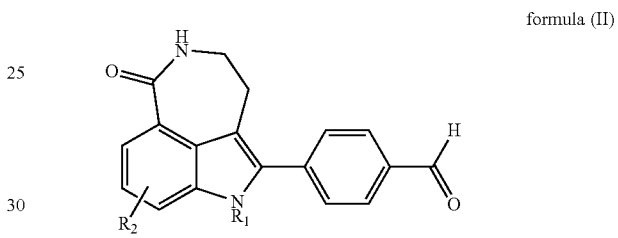

formula (II)

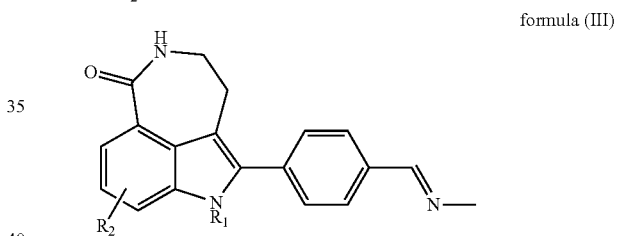

formula (III)

hydrogenating the compound of formula (III) under hydrogen to produce the tricyclic compound of formula (I) in the presence of a hydrogenation catalyst; wherein $R_1$ is H or a $C_{1-3}$ alkyl group; and $R_2$ is H, a halogen element or a $C_{1-3}$ alkyl group.

In one embodiment, the step of converting the compound of formula (II) into the compound of formula (III) comprises reacting the compound of formula (II) with methylamine to produce the compound of formula (III). Specifically, in some examples, equivalent ratio of the compound of formula (II) to methylamine is 1:1 to 1:5, for example, 1:1.5, 1:2, 1:2.5, 1:3, 1:3.5, 1:4 or 1:4.5. Furthermore, the reaction of the compound of formula (II) and methylamine solution is conducted at 20° C. to 40° C. in some embodiments.

In one embodiment, the hydrogenation catalyst in the step of hydrogenating the compound of formula (III) to produce the tricyclic compound of formula (I) is selected from at least one from the group consisting of Pd catalyst, Ni catalyst, Pt catalyst and Rh catalyst.

Specifically, in some embodiments, the hydrogenation catalyst is Pd/C catalyst and amount added into the reaction is 5% to 10% Pd/C. It is worth mentioning that the catalytic hydrogenation method used to replace reducing agent (e.g., NaBH$_3$CN, etc.) used conventionally to reduce imine compounds (i.e., the compound of formula (III)) and avoid from generating the toxic HCN gas.

It is to be appreciated that the step of converting the compound of formula (II) and the step of hydrogenating the compound of formula (III) are performed in succession without isolating the compound of formula (III) in the various embodiments of the present disclosure. In detail, the isolation step of the compound of formula (III) is not performed and the mixture which contains the compound of formula (III) directly transfers to reactor, and the compound of formula (III) in the mixture is hydrogenated in the presence of hydrogenation catalyst to produce the tricyclic compound of formula (I). Therefore, the target product may be obtained directly without isolation of intermediate product (i.e., the compound of formula (III)) by way of the method of the present disclosure. Accordingly, the step for purification and the loss of the intermediate product may be reduced, and the manufacturing process may be simplified, thereby effectively reducing cost and improving yield. In some embodiments, yield of the tricyclic compound of formula (I) formed by the step of converting the compound of formula (II) and hydrogenation the compound of formula (III) to produce the tricyclic compound of formula (I) is higher than 70%, for example, 71%, 72% or 84%.

In one embodiment of the step before converting the compound of formula (II), the method of the present disclosure further includes a following step: reacting a compound of formula (IV) with a compound of formula (V) to form the compound of formula (III);

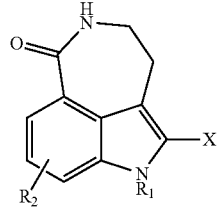

formula (IV)

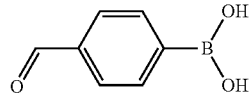

formula (V)

wherein X is a halogen element, such as fluorine, chlorine, bromine or iodine;

$R_1$ is H or a $C_{1-3}$ alkyl group; and $R_2$ is H, a halogen element or a $C_{1-3}$ alkyl group. Specifically, equivalent ratio of the compound of formula (IV) to the compound of formula (V) is 1:1 to 1:1.2 in some examples. In some examples, yield of the compound of formula (II) formed by reacting the compound of formula (IV) with the compound of formula (V) is 85% to 95%. For example, 87%, 89%, 92% or 93%.

In one embodiment of the step before reacting the compound of formula (IV) with the compound of formula (V), the present disclosure further comprises a following step: halogenating a following compound of formula (VI) to produce the compound of formula (IV);

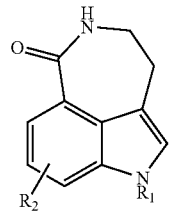

formula (VI)

wherein $R_1$ is H or a $C_{1-3}$ alkyl group; and $R_2$ is H, a halogen element or a $C_{1-3}$ alkyl group.

Specifically, the step of halogenating the compound of formula (VI) is performed by adding a halogenating agent. In some examples, the halogenating agent includes tetra-n-butylammonium tribromide, pyridinium tribromide, N-chlorosuccinimide, N-bromosuccinimide or N-iodosuccinimide, but not limiting herein. In some examples, equivalent ratio of the compound of formula (VI) to the halogenating agent is 1:1 to 1:2. In some examples, halogenating the compound of formula (VI) is performed at 0° C. to 20° C., such as 5° C., 10° C. or 15° C. Further, yield of the compound of formula (IV) formed by halogenating the compound of formula (VI) is 85% to 95%, for example 87%, 89%, 91% or 93%.

In one embodiment of the step before halogenating the compound of formula (VI), the present disclosure further comprises a following step:
converting a following compound of formula (VII) to form the compound of formula (VI);

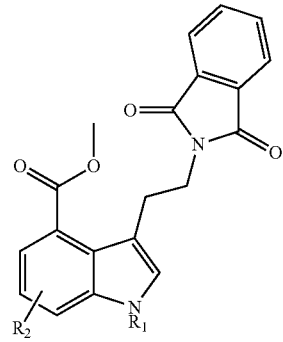

formula (VII)

wherein $R_1$ is H or a $C_{1-3}$ alkyl group; and $R_2$ is H, a halogen element or a $C_{1-3}$ alkyl group.

In one embodiment, the step of converting the compound of formula (VII) into the compound of formula (VI) comprises reacting the compound of formula (VII) with methylamine to form the compound of formula (VI). Specifically, equivalent ratio of the compound of formula (VII) to methylamine is 1:1.5 to 1:3.0 in some examples. In some examples, converting the compound of formula (VII) is performed at 15° C. to 40° C., such as 20° C., 25° C., 30° C. or 35° C. In addition, in some examples, yield of the compound of formula (VI) formed by converting the compound of formula (VII) is 87% to 97%, for example 89%, 91%, 93% or 94%.

In one embodiment of the step before converting the compound of formula (VII), the present disclosure further comprises a following step: reacting a compound of formula (VIII) with a compound of formula (IX) to produce the compound of formula (VII);

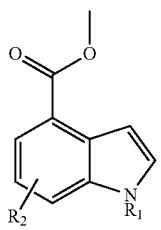

formula (VIII)

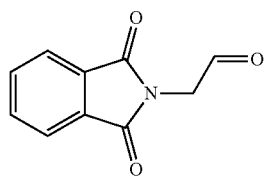

formula (IX)

wherein R$_1$ is H or a C$_{1-3}$ alkyl group; and
R$_2$ is H, a halogen element or a C$_{1-3}$ alkyl group.

In some embodiments, equivalent ratio of the compound of formula (VIII) to the compound of formula (IX) is 1:1.1 to 1:1.5, such 1:1.2, 1:1.3 or 1:1.4. In some examples, the reaction of the compound of formula (VIII) and the compound of formula (IX) is performed at 15° C. to 40° C., such as 20° C., 25° C., 30° C. or 35° C. In addition, in some examples, yield of the compound of formula (VII) formed by the reacting the compound of formula (VIII) with the compound of formula (IX) is 50% to 60%, for example 51%, 53%, 55% or 57%.

Another embodiment of the present disclosure provides a method of preparing of a following tricyclic compound (the salt form of PARP inhibitor) of formula (X),

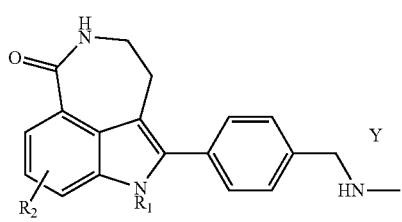

formula (X)

wherein Y is a pharmaceutically acceptable acid;
R$_1$ is H or a C$_{1-3}$ alkyl group; and
R$_2$ is H, a halogen element or a C$_{1-3}$ alkyl group.

In some examples, the pharmaceutically acceptable acids includes phosphoric acid, hydrochloric acid, ethanedisulfonic acid, acetic acid, benzenesulfonic acid, benzoic acid, camphorsulfonic acid, citric acid, fumaric acid, maleic acid, malic acid, oxalic acid, tartaric acid, or the like but not limiting herein. Preferably, in one example, the pharmaceutically acceptable acid is camphorsulfonic acid.

The method of preparing the tricyclic compound of formula (X) includes the following steps: reacting the above described tricyclic compound of formula (I) with the pharmaceutically acceptable acid to form the tricyclic compound of formula (X).

In addition, in some examples, equivalent ratio of the tricyclic compound of formula (I) to the pharmaceutically acceptable acid is 1:1.1 to 1:1.3. In some examples, the reaction of the tricyclic compound of formula (I) and the pharmaceutically acceptable acid is performed at 65° C. to 85° C., for example 68° C., 70° C., 73° C., 77° C. or 81° C.

Further, in some examples, yield of the compound of formula (X) formed by reacting the compound of formula (I) with the pharmaceutically acceptable acid is 76% to 86%, for example 78%, 80%, 81% or 84%.

In one embodiment, the tricyclic compound of formula (X) includes the Rucaparib (S)-camphorsulfonate salt with structure of formula (5).

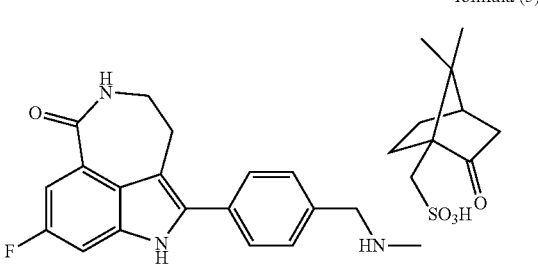

formula (5)

In some examples, the Rucaparib (S)-camphorsulfonate salt is in a crystalline form. In one specific example, X-ray powder diffraction pattern of the crystalline of the Rucaparib (S)-camphorsulfonate salt of formula (5) comprising characteristic peaks at two theta values of 6.0°±0.2°, 6.2°±0.2°, 12.2°±0.2° and 13.5°±0.2°. In another specific example, X-ray powder diffraction pattern of crystalline of the Rucaparib (S)-camphorsulfonate salt of formula (5) comprising characteristic peaks at two theta values of 6.0°±0.2°, 6.2°±0.2°, 12.0°±0.2°, 12.2°±0.2°, 13.5°±0.2° and 25.7°±0.2°. In one specific example, melting point of crystalline of the Rucaparib (S)-camphorsulfonate salt is about 304±2° C.

In one embodiment, the method of preparing of crystalline of the Rucaparib (S)-camphorsulfonate salt of formula (5) comprises the step of reacting the (S)-camphorsulfonate salt with the Rucaparib of formula (1) within methanol/water solution to produce the Rucaparib (S)-camphorsulfonate salt of formula (5); and filtrating a crystalline of the Rucaparib (S)-camphorsulfonate salt of formula (5) from methanol/water solution.

Figure 2:
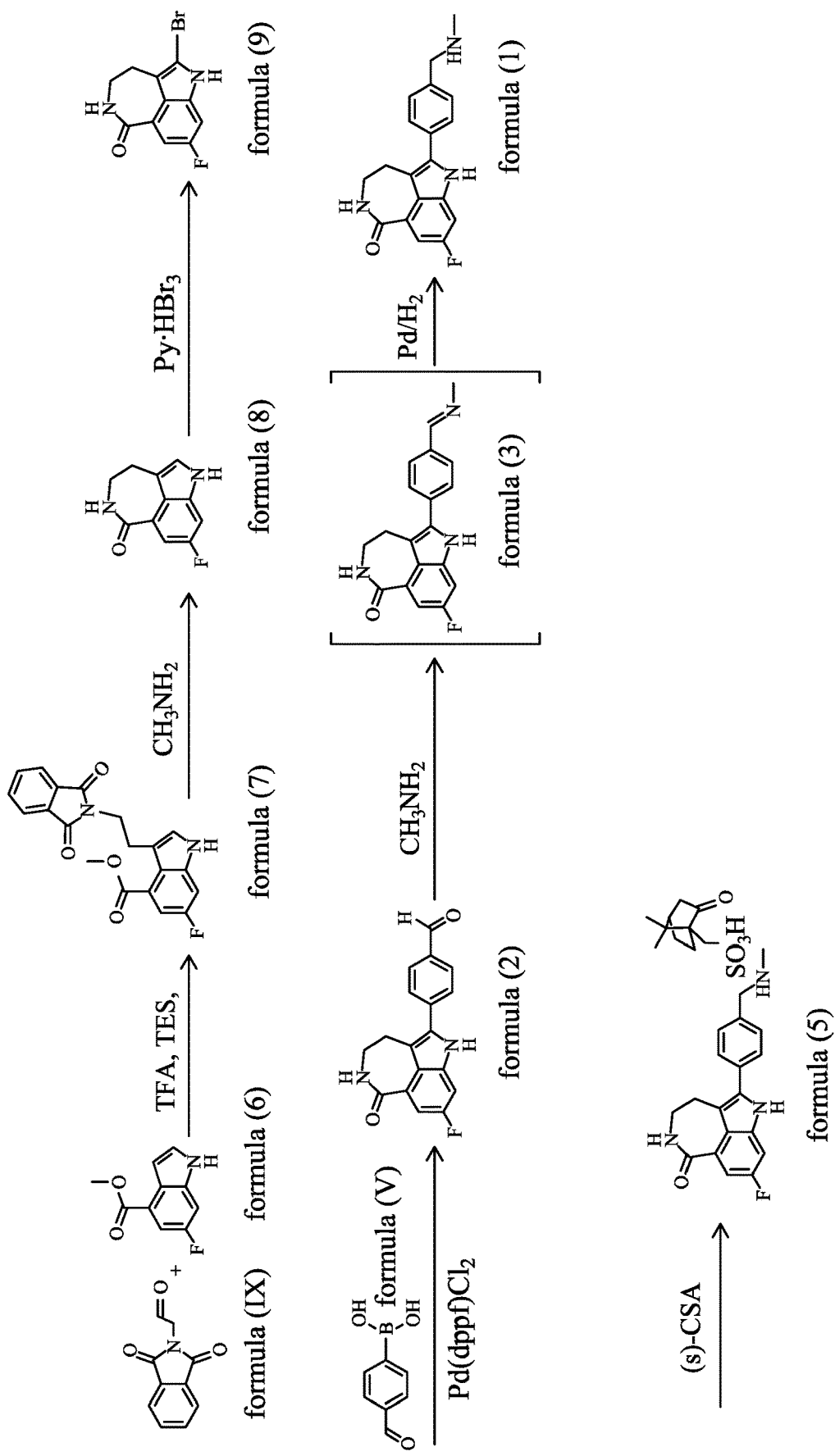
FIG. 2 is a synthesis scheme of Rucaparib (S)-camphorsulfonate salt, in accordance with one embodiment of the present disclosure.

Referring to FIG. 2, FIG. 2 shows a view of synthesis scheme of the Rucaparib with structure of formula (1) and the Rucaparib (S)-camphorsulfonate salt with structure of formula (5) in one embodiment of the present disclosure.

In one embodiment of the present disclosure, a compound of formula (6) is acted as a starting material for the reaction with the compound of formula (IX) to obtain a compound of formula (7). Then the compound of formula (7) is converted to form a compound of formula (8). The compound of formula (8) is halogenated to form a compound of formula (9). The compound of formula (9) is subsequently reacted with the compound of formula (V) to form the compound of formula (2). Next, the compound of formula (2) is converted to form the compound of formula (3). The compound of formula (3) is hydrogenated under hydrogen in the presence of hydrogenation catalyst to produce the Rucaparib of formula (1). Finally, Rucaparib with the structure of formula (1) is reacted with camphorsulfonic acid to produce the Rucaparib (S)-camphorsulfonate salt with the structure of formula (5).

The following examples are now exemplified to illustrate the method of preparing of PARP inhibitor in detail and its salt form in the present disclosure. However, the following examples are not limiting in the present disclosure.

Example 1: Preparing of the Compound of Formula (7)

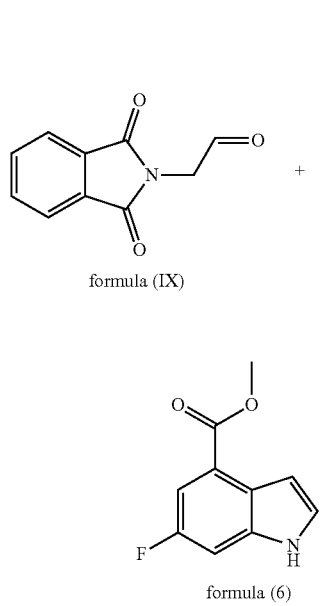

formula (IX)

formula (6)

TFA, TES → formula (7)

2-(1,3-dioxoisoindolin-2-yl)acetaldehyde (2-DAA, i.e., the compound of formula (IX), 191.0 g, 1.3 eq.) and 6-fluoro-1H-indole-4-carboxylic acid methyl ester (6-FI-CAME, i.e., the compound of formula (6), 150.0 g, 1 eq.) in dichloromethane ($CH_2Cl_2$, 997.5 g) was added with triethylsilane (TES, 361.4 g, 4 eq.) and the mixture was stirred at room temperature. A solution of trifluoroacetic acid (TFA, 180.0 g, 2 eq.) in dichloromethane ($CH_2Cl_2$, 399.0 g) was added into the above mixture at 8° C. and kept stirring for 2 hours. Afterwards, it was stirred at room temperature for 86 hours and cooled to about 8° C. for another 2 hours. After filtrating, the solid were washed with $CH_2Cl_2$ and was added into ethyl acetate (EA). The mixture was heated to reflux for 2 hours and cooled to room temperature. After filtrating, the solids were washed with EA and dried under vacuum to obtain 3-(2-(phthalimido)ethyl)-6-fluoro-1H-indole-4-carboxylic acid methyl ester (i.e., the compound of formula (7), 157.16 g, 55%).

Example 2: Preparing of the Compound of Formula (8)

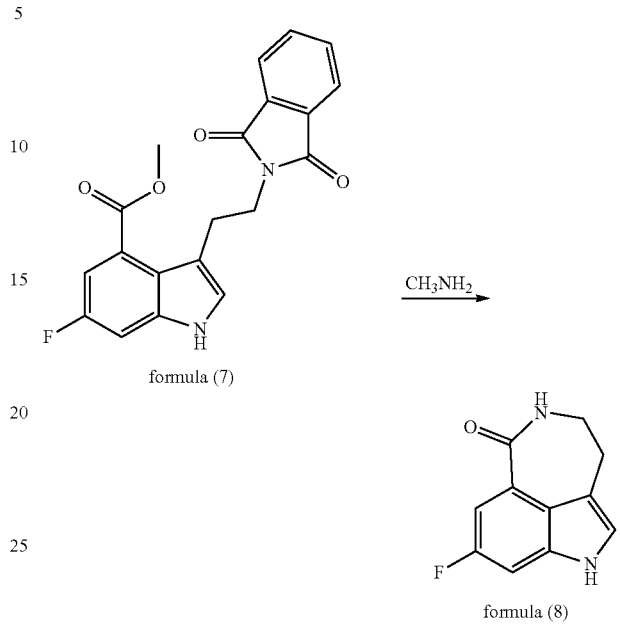

formula (7)

$CH_3NH_2$ → formula (8)

The compound of formula (7) (157.0 g, 1.0 eq.) was added to methylamine aqueous solutions (40% $MeNH_2$ in $H_2O$) (563.3 g) to form a mixture, and the mixture was stirred at room temperature for 24 hours. The deionized water (1099.0 g) was added into the mixture. Afterwards, the mixture was cooled to 0° C. to 5° C. and stirred for 2 hours. After filtrating, the solid was washed with the deionized water for three times and dried under vacuum to obtain 8-fluoro-1,3,4,5-tetrahydro-6H-azepino[5,4,3-cd]indol-6-one (i.e., the compound of formula (8), 82.2 g, 94%).

Example 3: Preparing of the Compound of Formula (9)

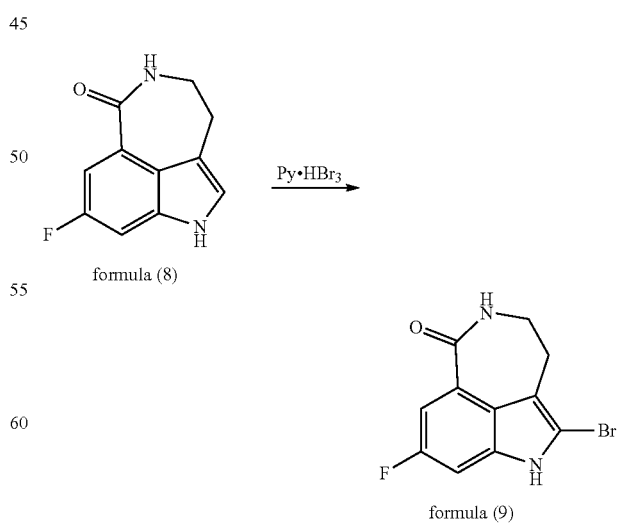

formula (8)

Py·$HBr_3$ → formula (9)

The compound of formula (8) (77.60 g, 1.0 eq.) in $CH_2Cl_2$ (387.0 g) and THF (257.8 g) was added with pyridinium tribromide (Py·HBr₃, 133.5 g, 1.1 eq.) at 10° C. The above mixture was stirred at 15° C. to 20° C. for 1 hour. The mixture was cooled to 10° C., the deionized water (194.0 g) was added into the mixture to quench the reaction. The above mixture was concentrated under vacuum with temperature not higher than 20° C. The residue was sequentially added with THF (54.9 g), deionized water (194.0 g) and 20% Na₂CO₃ solution (69.8 g Na₂CO₃ in 279.4 g water) with temperature not higher than 20° C. and the mixture was stirred to neutralize the generated acid. After filtrating the mixture, the solid was washed with deionized water for three times and dried under vacuum to obtain 2-bromo-8-fluoro-1,3,4,5-tetrahydro-6H-azepino[5,4,3-cd]-indol-6-one (i.e., the compound of formula (9), 98.1 g, 91%).

Example 4: Preparing of the Compound of Formula (2)

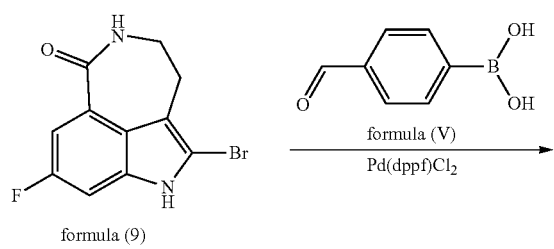

The compound of formula (9) (97.5 g) in dimethylacetamide (DMAc, 549.9 g) was added with Pd(dppf)Cl₂ ([1,1'-Bis(diphenylphosphino)ferrocene] dichloropalladium(II), (7.0 g) at room temperature. The mixture was heated to 90° C. to 95° C. and stirred for 1 hour to form the first solution. 4-formylphenylboronic acid (4-FPBA, 62.0 g) in dimethylacetamide (DMAc, 183.3 g) was stirred and 7% Na₂CO₃ solution (73.0 g Na₂CO₃ in 975.0 g water) was added into the above mixture to form the second solution. The second solution was added into the first solution at 93° C. under nitrogen atmosphere to form the third solution and it was heated to 98° C. for 1 hour and then was cooled to 88° C. The deionized water (1950.0 g) was added into the third solution and stirred at room temperature for 1 hour. After filtrating, the solid was washed with deionized water. The residue was added with MeOH (616.2 g) and heated to reflux for 1 hour and cooled to room temperature with stirring for another hour. After filtrating, the solid was washed with MeOH, and dried under vacuum to obtain 4-(8-fluoro-6-oxo-3,4,5,6-tetrahydro-1H-azepino[5,4,3-cd] indol-2-yl)-benzaldehyde (i.e., the compound of formula (2), 97.8 g, 92%).

Example 5-1: Preparing of Rucaparib of Formula (1)

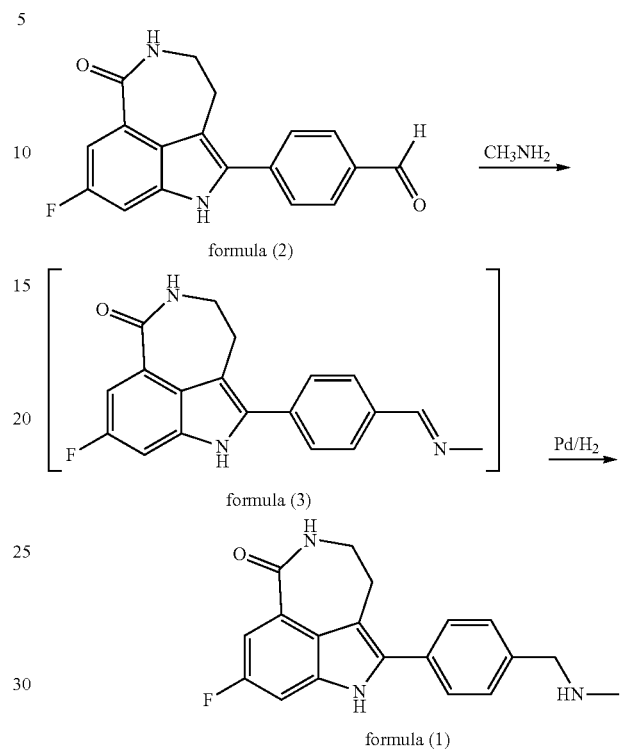

The compound of formula (2) (50.0 g) in MeOH (437.0 g) and THF (223.0 g) with stirring at 25° C. was added with 30% CH₃NH₂ solution (in EtOH) (34.0 g) and kept stirring at 33° C. for 8 hours. The mixture was transferred to Hydrogenation reactor with 5% of Pd/C (10.5 g) therein to proceed hydrogenation. The reaction mixture was filtrated and the solid was washed with MeOH/THF=2.2/1 and with MeOH and dried under vacuum to obtain Rucaparib of formula (1) (37.9 g, 72%).

Example 5-2: The Preparing of Rucaparib of Formula (1)

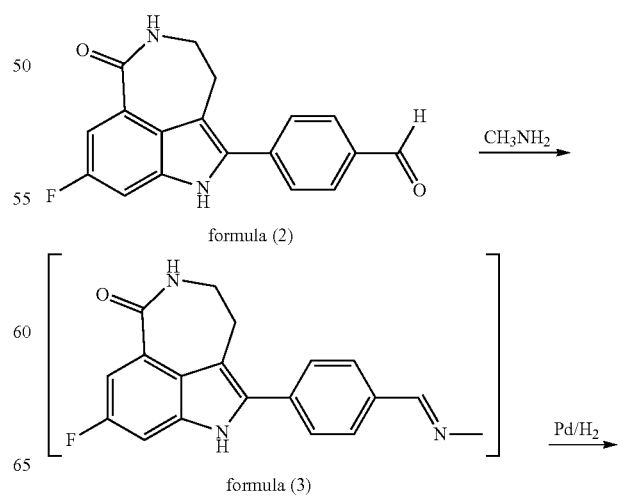

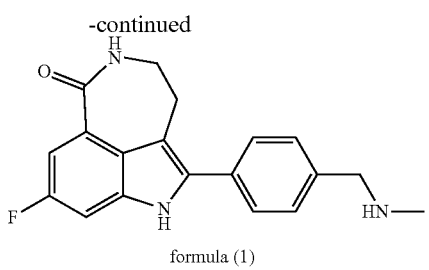

formula (1)

The compound of formula (2) (35.0 g) in MeOH (305.5 g) and THF (156.0 g) with stirring at 25° C. was added with 30% CH$_3$NH$_2$ solution (in EtOH) (35.3 g) and kept stirring at 33° C. for 12 hours. The mixture was transferred to Hydrogenation reactor with 10% of Pd/C (7.25 g) therein to proceed hydrogenation. The reaction mixture was filtrated and the solid was washed with MeOH and dried under vacuum to obtain Rucaparib of formula (1) (30.8 g, 84%).

Example 5-3: Preparing of Rucaparib of Formula (1)

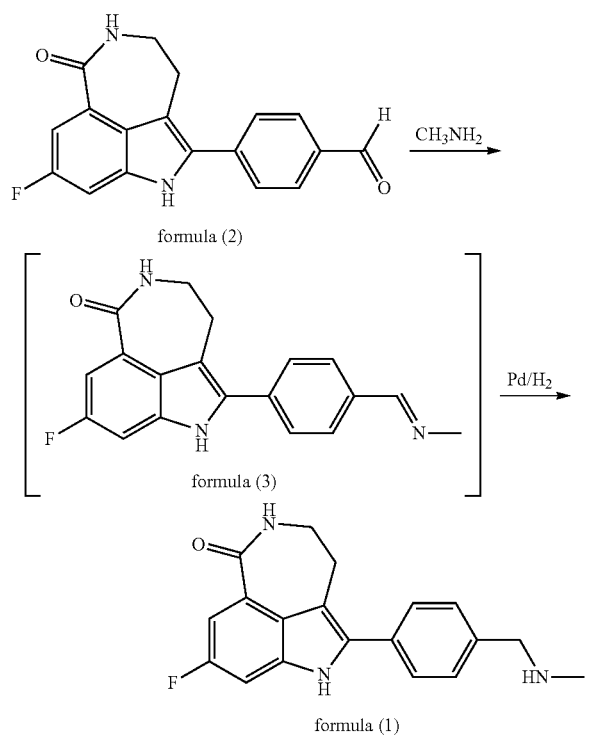

The compound of formula (2) (76.5 g) in MeOH (665.0 g) and THF (339.0 g) with stirring at 25° C. was added with 30% CH$_3$NH$_2$ solution (in EtOH) (52.0 g) and kept stirring at 33° C. for 8 hours. The mixture was transferred to Hydrogenation reactor with 10% of Pd/C (8.04 g) therein to proceed hydrogenation. The active carbon (3.82 g) was added into the mixture with stirring at 40° C. for 2 hours. After filtrating, the solid was washed with MeOH and dried under vacuum to obtain Rucaparib of formula (1) (57.0 g, 71%).

As described above, the method of the present disclosure may be used to reduce the step of purification and the loss of the intermediate product. To be more specific that as shown in examples 5-1 to 5-3, the isolation step of the compound of formula (3) is not conducted and the generated mixture is directly hydrogenated to form Rucaparib of formula (1). In other words, the method of the present disclosure, compared to the conventional synthesis scheme (as shown in FIG. 1), omits for forming the compound of formula (4) and final neutralization step thereof to avoid the loss of the intermediate product.

Further, it is worth mentioning that in conventional synthesis scheme (as shown in FIG. 1), NaBH$_3$CN as a reducing agent is used to react with the compound of formula (3), and then hydrochloric acid solution is added into the reaction to form salt, in final potassium hydroxide solution is added to neutralize the reaction to give Rucaparib. The intermediate product of formula (4) (i.e., hydrochloride salt of Rucaparib) is also formed by conventional synthesis scheme in contrast to the method of the present disclosure. Accordingly, the conversional process for the compound of formula (4) is required more steps thereby to cause yield loss during converting the compound of formula (4) to Rucaprib.

In order to facilitate understanding the advantage of the present disclosure, the yields of Examples 5-1 to 5-3 and the yield of formation of Rucaparib of formula (1) formed with the conventional synthesis scheme are reported in Table 1 below.

TABLE 1

|  | Reaction reagent | Yield |
| --- | --- | --- |
| Conventional synthesis scheme | As shown in FIG. 1 | 31% |
| Example 5-1 | 2.0 eq. CH$_3$NH$_2$, 5% Pd/C H$_2$ | 72% |
| Example 5-2 | 4.0 eq. CH$_3$NH$_2$, 10% Pd/C H$_2$ | 84% |
| Example 5-3 | 2.0 eq. CH$_3$NH$_2$, activated carbon and 10% Pd/C H$_2$ | 71% |

From the contents of Table 1, it is known that the synthesis of Rucaparib of formula (1) with the conventional synthesis scheme as shown in FIG. 1 requires to more synthetic steps and purification, resulting in more yield loss. In contrast, the method of examples 5-1 to 5-3 is applied to synthesize Rucaparib of formula (1), with not only its yields higher than 70%, even up to 84%, but also simplifying the synthesis step.

Example 6: Preparing of Crystalline of the Rucaparib (S)-camphorsulfonate Salt of Formula (5)

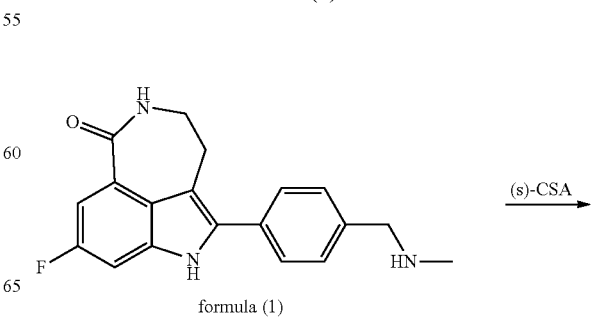

formula (1)

-continued

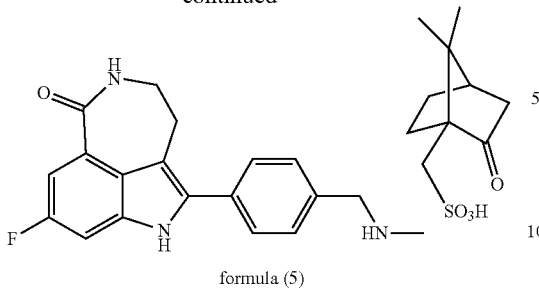

formula (5)

Rucaparib of formula (1) (75.00 g) in MeOH (685.38 g) and H₂O (204.42 g) with stirring was added with (S)-Camphorsulfonic acid (CSA, 64.50 g) in H₂O (55.19 g) and heated to reflux for 1 hour. After hot filtration, the filtrate was heated to reflux and gradually cooled to 40° C. for 8 hours and to room temperature for 8 hours and to 0° C. to 5° C. for another 12 hours. After filtrating, the solids were washed with H₂O, and dried under vacuum to obtain crystalline of the Rucaparib (S)-camphorsulfonate salt of formula (5) (1.36 g, 81%).

Figure 3:
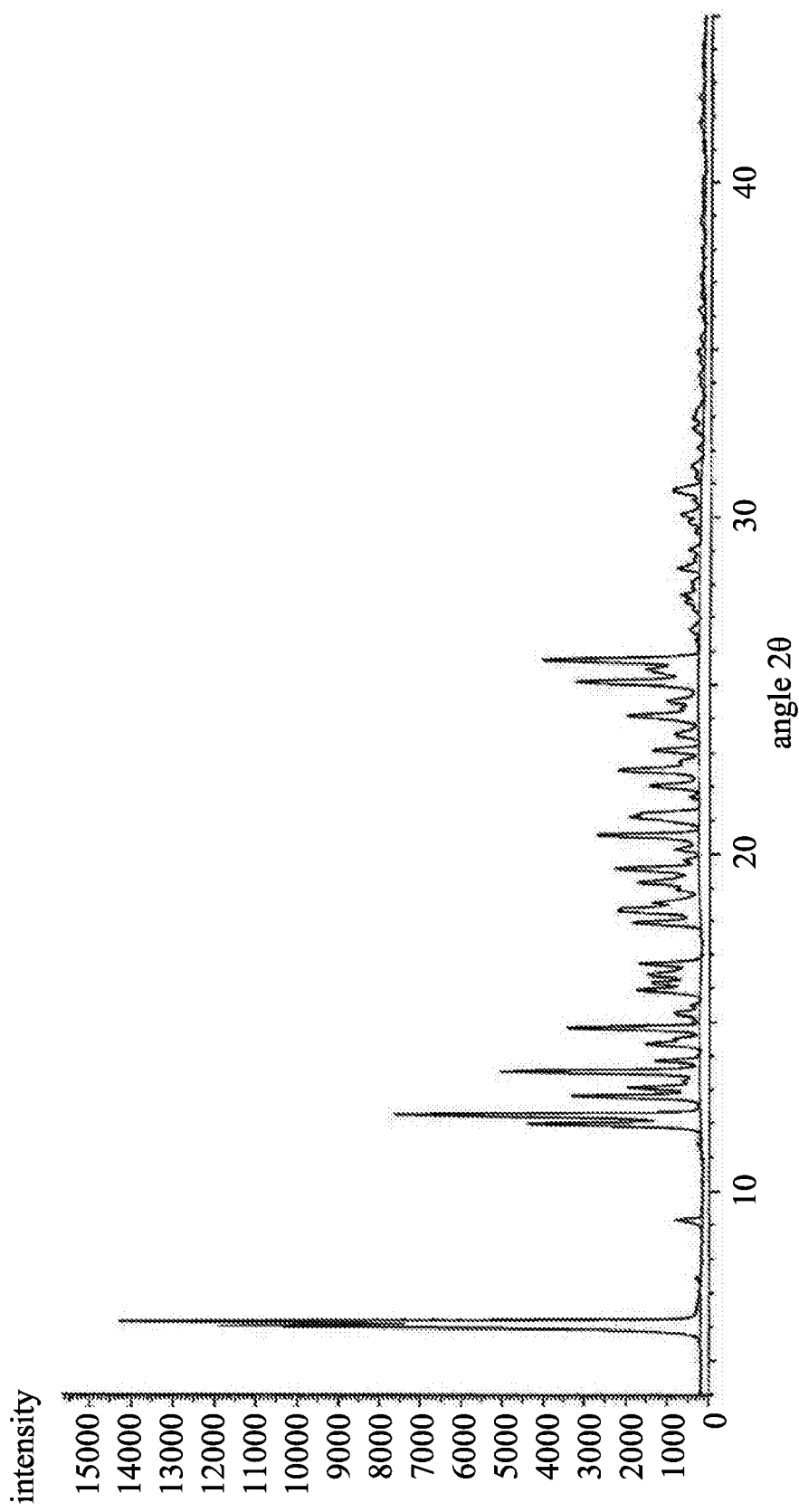
FIG. 3 is a X-ray powder diffraction pattern of crystalline of the Rucaparib (S)-camphorsulfonate salt, in accordance with one embodiment of the present disclosure.

Example 7: Determination of X-Ray Powder Diffraction Pattern of Crystalline of the Rucaparib (S)-camphorsulfonate Salt X-ray diffraction spectrometer (Bruker D8 Advance) is used to determine X-ray powder diffraction pattern of crystalline of the Rucaparib (S)-camphorsulfonate salt of formula (5) to obtain X-ray powder diffraction pattern as shown in FIG. 3. Specifically, X-ray powder diffraction pattern is obtained by use of copper K-α1X-ray at a wavelength of 1.5406 Angstrom, and the parameters for measurement are shown in Table 2 below.

TABLE 2

| XRD parameter | |
|---|---|
| Scan type | Normal |
| Voltage | 40 kV |
| Current | 40 mA |
| Scan range (2θ) | 4° to 45° |
| Step size | 0.02° |
| Time (sec) | 0.5 |

In FIG. 3, characteristic peaks with relative intensity ≥10.0% and corresponding diffraction angles degrees (2θ) thereof are described in Table 3 below.

TABLE 3

| Diffraction angle ((2θ) ± 0.2) | Relative intensity (≥10.0%) |
|---|---|
| 6.0 | 85.0% |
| 6.2 | 100% |
| 12.0 | 30.6% |
| 12.2 | 54.5% |
| 12.8 | 22.3% |
| 13.1 | 12.6% |
| 13.5 | 34.6% |
| 14.8 | 23.2% |
| 16.0 | 11.2% |
| 16.7 | 10.9% |
| 18.0 | 12.1% |
| 18.3 | 14.3% |
| 19.2 | 10.7% |
| 19.6 | 14.6% |
| 20.6 | 17.9% |
| 21.1 | 12.4% |
| 21.2 | 10.6% |
| 22.5 | 14.0% |
| 24.1 | 12.4% |
| 25.1 | 21.4% |
| 25.7 | 27.5% |

Figure 4:
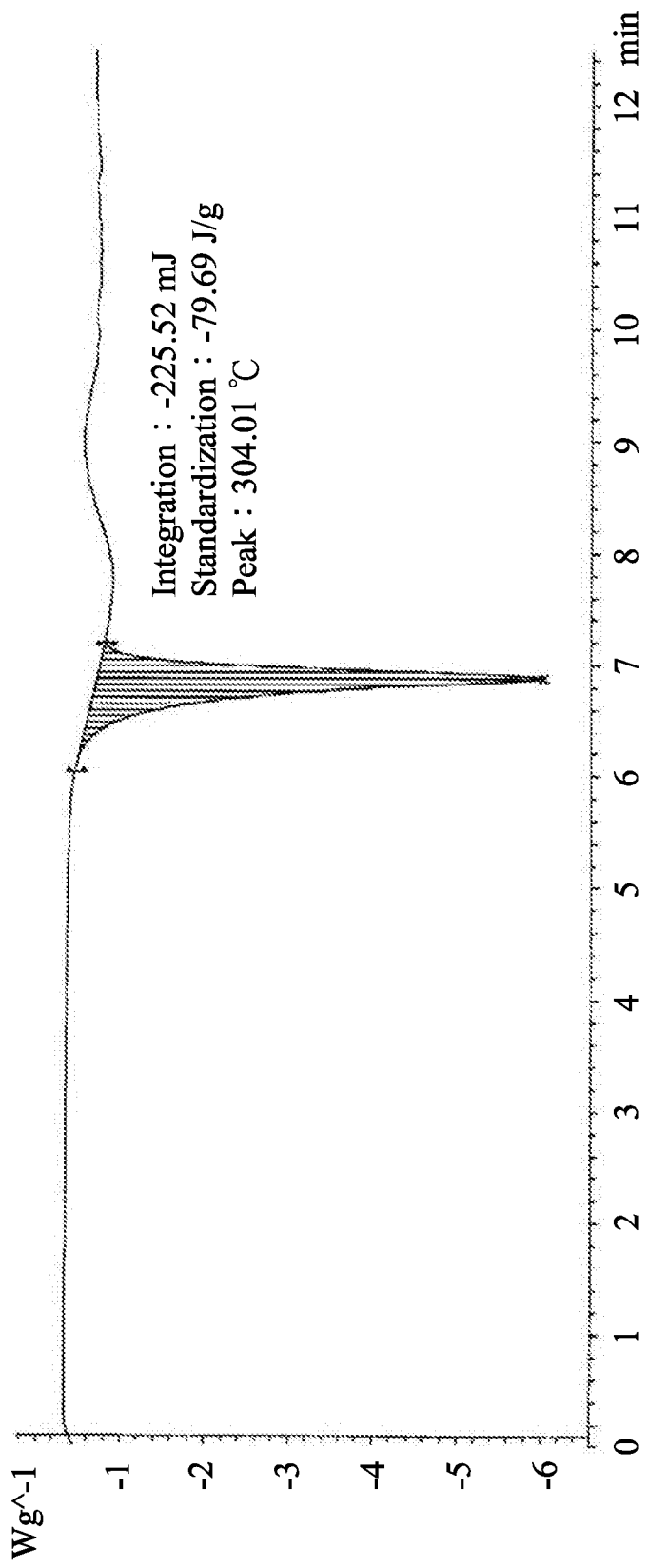
FIG. 4 is a differential scanning calorimetry (DSC) spectrum of crystalline of the Rucaparib (S)-camphorsulfonate salt, in accordance with one embodiment of the present disclosure.

Example 8: Differential Scanning Thermal Analysis of Crystalline of the Rucaparib (S)-camphorsulfonate Salt Differential scanning thermal analysis of crystalline of the Rucaparib (S)-camphorsulfonate of formula (5) is performed by use of differential scanning calorimeter (Mettler_Toledo DSC 2 STARe system) to obtain differential scanning thermal analysis spectrum as shown in FIG. 4. Operation parameter: 250° C. to 350° C.; 8° C./min; N₂ 60.0 mL/min.

As shown in FIG. 4, the melting point of crystalline of the Rucaparib (S)-camphorsulfonate is about 304±2° C. (having a peak at about 304° C.).

In summary, the method of preparing PARP inhibitor, the salt thereof and the crystalline form thereof disclosed herein are more simplified than the conventional process in saving reaction time and effectively improving overall yield. Further, generation of toxic gas such as HCN is avoided since without using NaBH₃CN as reducing agent, the method of the present disclosure is therefore suitable for mass production.

Although the present invention has been described in considerable detail with reference to certain embodiments thereof, other embodiments are possible. Therefore, the scope of the claims and the scope of the claims are not limited to the description contained in the embodiments herein.

It will be apparent to those skilled in the art that various modifications and variations can be made to the structure of the present invention without departing from the scope of the invention. In view of the foregoing, it is intended that the present invention cover modifications and variations of this invention provided they fall within the scope of the following claims.

What is claimed is:

1. A method of preparing a tricyclic compound of formula (I):

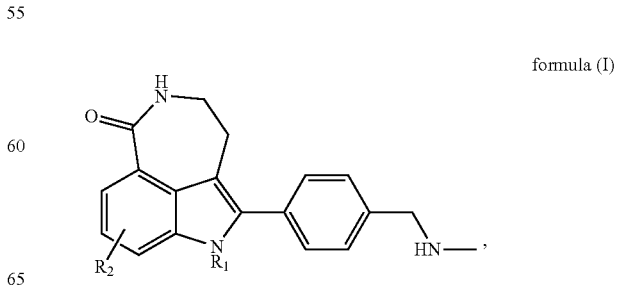

formula (I)

the method comprising steps of:
converting a compound of formula (II) into a compound of formula (III); and

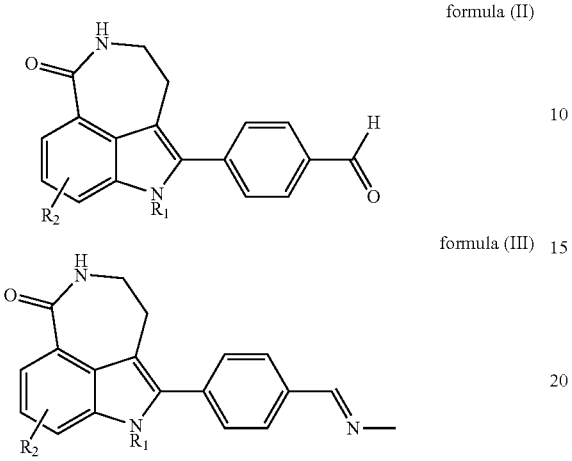

formula (II)

formula (III)

hydrogenating the compound of formula (III) under hydrogen to produce the tricyclic compound of formula (I) in the presence of a hydrogenation catalyst;
wherein $R_1$ is H or a $C_{1-3}$ alkyl group; and
$R_2$ is H, a halogen element or a $C_{1-3}$ alkyl group.

2. The method of claim 1, wherein the step of converting the compound of formula (II) into the compound of formula (III) comprises reacting the compound of formula (II) with methylamine to form the compound of formula (III).

3. The method of claim 1, wherein the hydrogenation catalyst is at least one selected from the group consisting of Pd catalyst, Ni catalyst, Pt catalyst and Rh catalyst.

4. The method of claim 1, wherein the step of converting the compound of formula (II) and the step of hydrogenating the compound of formula (III) are performed in succession without isolating the compound of formula (III).

5. The method of claim 1, wherein before the step of converting the compound of formula (II), further comprising a step of:
reacting a compound of formula (IV) with a compound of formula (V) to form the compound of formula (II);

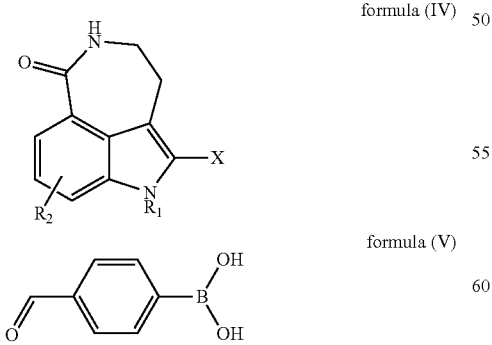

formula (IV)

formula (V)

wherein $R_1$ is H or a $C_{1-3}$ alkyl group;
$R_2$ is H, a halogen element or a $C_{1-3}$ alkyl group; and
X is a halogen element.

6. The method of claim 5, wherein before the step of reacting the compound of formula (IV) with the compound of formula (V), further comprising a step of:
halogenating a compound of formula (VI) to produce the compound of formula (IV);

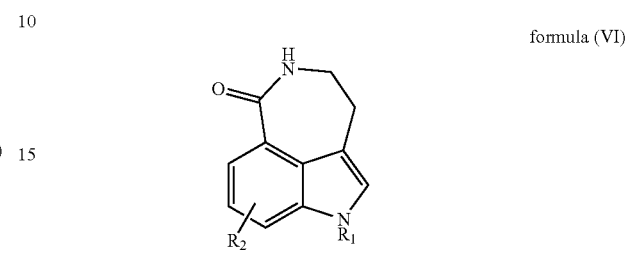

formula (VI)

wherein $R_1$ is H or a $C_{1-3}$ alkyl group; and
$R_2$ is H, a halogen element or a $C_{1-3}$ alkyl group.

7. The method of claim 6, wherein before the step of halogenating the compound of formula (VI), further comprising a step of:
converting a compound of formula (VII) into the compound of formula (VI);

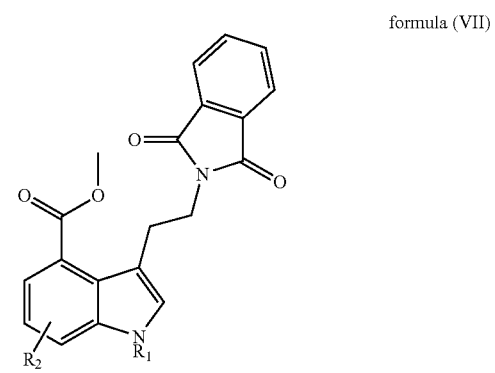

formula (VII)

wherein $R_1$ is H or a $C_{1-3}$ alkyl group; and
$R_2$ is H, a halogen element or a $C_{1-3}$ alkyl group.

8. A method of preparing a tricyclic compound of formula (X),

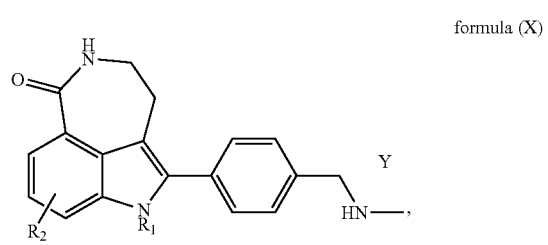

formula (X)

the method comprising steps of:
preparing a tricyclic compound of formula (I) using the method of claim 1; and formula (I)

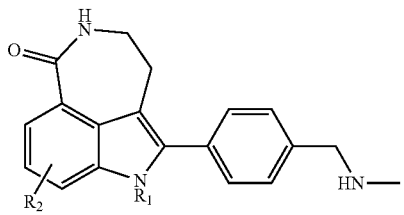

reacting the tricyclic compound of formula (I) with a pharmaceutically acceptable acid to form the tricyclic compound of formula (X);

wherein $R_1$ is H or a $C_{1-3}$ alkyl group;

$R_2$ is H, a halogen element or a $C_{1-3}$ alkyl group; and

Y is a pharmaceutically acceptable acid.

9. The method of claim 8, wherein the pharmaceutically acceptable acid is camphorsulfonic acid.

10. A method of preparing Rucaparib of formula (I), formula (I)

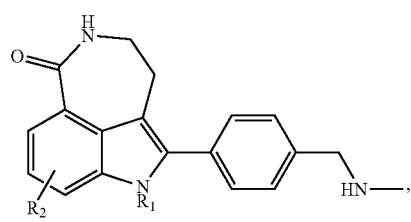

wherein $R_1$ is H and $R_2$ is F;

the method comprising steps of:

reacting a compound of formula (6) with a compound of formula (IX) to produce a compound of formula (7);

formula (6)

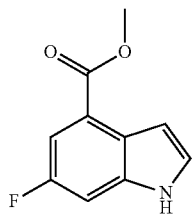

formula (IX)

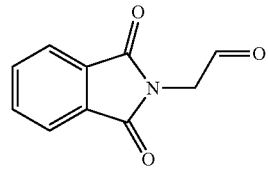

formula (7)

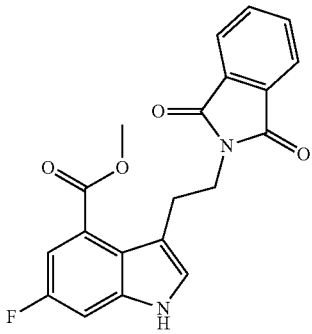

converting the compound of formula (7) to a compound of formula (8);

formula (8)

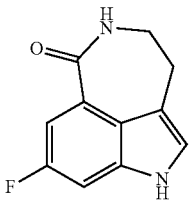

converting the compound of formula (8) to a compound of formula (9);

formula (9)

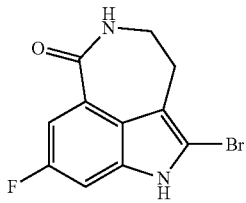

reacting the compound of formula (9) with a compound of formula (V) to form a compound of formula (2);

formula (V)

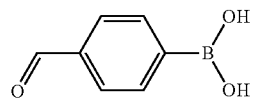

formula (2)

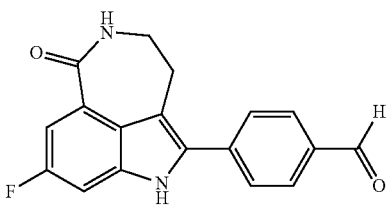

converting the compound of formula (2) to a compound of formula (3); and

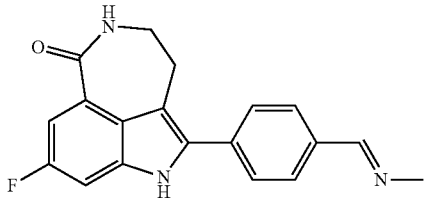

formula (3)

hydrogenating the compound of formula (3) under hydrogen in the presence of hydrogenation catalyst to prepare the Rucaparib of formula (1).

11. A method of preparing a tricyclic compound of formula (X),

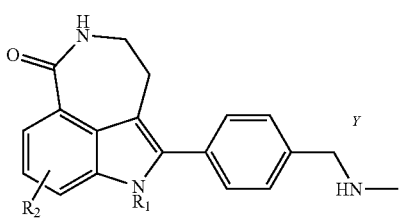

formula (X)

the method comprising steps of:

preparing a tricyclic compound of formula (I) using the method of claim 1; and

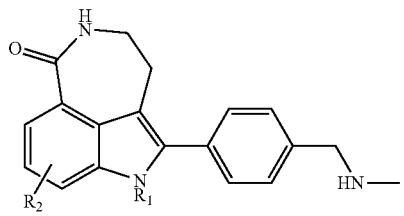

formula (I)

reacting the tricyclic compound of formula (I) with a pharmaceutically acceptable acid to form the tricyclic compound of formula (X);

wherein $R_1$ is H;

$R_2$ is F; and

Y is a camphorsulfonic acid;

wherein a crystalline of the tricyclic compound of formula (X) has an X-ray powder diffraction pattern comprising characteristic peaks at two theta values of 6.0°±0.20°, 6.2°±0.20°, 12.2°±0.2° and 13.5°±0.2°.

12. The method of claim 11, wherein the X-ray powder diffraction pattern further comprises characteristic peaks at two theta values of 12.0°±0.2° and 25.7°±0.2°.

13. The method of claim 11, wherein the X-ray powder diffraction pattern is substantially the same as that shown in FIG. 3.

14. The method of claim 11, wherein the melting point of the tricyclic compound of formula (X) is about 304±2° C.

15. The method of claim 11, wherein the crystalline of the tricyclic compound of formula (X) is formed when reacting the tricyclic compound of formula (I) with camphorsulfonic acid in a methanol/water solution.

* * * * *